United States Patent
Eiben et al.

(10) Patent No.: US 10,299,484 B2
(45) Date of Patent: May 28, 2019

(54) COMPOSITION ESSENTIALLY FREE OF WATER AND COMPRISING AT LEAST ONE SPORE FORMING FUNGAL BIOLOGICAL CONTROL AGENT, A POLYETHER-MODIFIED TRISILOXANE AND FUMED OR PRECIPITATED SILICA

(71) Applicant: Bayer CropScience Biologics GmbH, Wismar (DE)

(72) Inventors: Ute Eiben, Malchow/Poel (DE); Marion Karge, Wismar (DE); Peter Lüth, Wismar (DE); Beata-Maria Lortz, Hanau-Wolfgang (DE)

(73) Assignee: Bayer CropScience Biologics GmbH, Wismar (DE)

( * ) Notice: Subject to any disclaimer, the term of this patent is extended or adjusted under 35 U.S.C. 154(b) by 0 days.

(21) Appl. No.: 15/516,049

(22) PCT Filed: Sep. 29, 2015

(86) PCT No.: PCT/EP2015/072346
§ 371 (c)(1),
(2) Date: Mar. 31, 2017

(87) PCT Pub. No.: WO2016/050726
PCT Pub. Date: Apr. 7, 2016

(65) Prior Publication Data
US 2017/0295799 A1    Oct. 19, 2017

(30) Foreign Application Priority Data

Oct. 2, 2014  (EP) .................................... 14187473
Nov. 20, 2014 (EP) .................................... 14194071

(51) Int. Cl.
*A01N 63/04*    (2006.01)

(52) U.S. Cl.
CPC .................................... *A01N 63/04* (2013.01)

(58) Field of Classification Search
None
See application file for complete search history.

(56) References Cited

U.S. PATENT DOCUMENTS 9,788,551 B2 * 10/2017  Luth .................. A01N 63/00

FOREIGN PATENT DOCUMENTS

| WO | 2009/126473 A1 | 10/2009 |
| WO | 2012/163322 A1 | 12/2012 |
| WO | 2013/181738 A1 | 12/2013 |

OTHER PUBLICATIONS

Küçük, C., et al., "Effect of Formulation of the Viability of Biocontrol Agent, Trichoderma harzianum conidia," African Journal of Biotechnology, Jun. 2005, vol. 4, No. 5, pp. 483-486.
Schisler, D.A., "Formulation of *Bacillus* spp. for Biological Control of Plant Diseases," Phytopathology, 2004, vol. 94, No. 11, pp. 1267-1271.
Torres, et al., "Liquid Formulation of the Biocontrol Agent Candida sake by Modifying Water Activity or Adding Protectants," Journal of Applie Microbiology, 2003, vol. 94, No. 2, pp. 330-339.
International Search Report and Written Opinion of the International Searching Authority for International Patent Application No. PCT/EP2015/072346, dated Feb. 18, 2016, 9 pages.

* cited by examiner

*Primary Examiner* — Alton N Pryor

(57) ABSTRACT

The present invention relates to a liquid composition comprising at least one biological control agent wherein said biological control agent is spores of a spore forming fungus, a polyether-modified trisiloxane and fumed silica or precipitated silica, wherein said composition is essentially free of water, said composition being useful in plant protection.

21 Claims, No Drawings

COMPOSITION ESSENTIALLY FREE OF WATER AND COMPRISING AT LEAST ONE SPORE FORMING FUNGAL BIOLOGICAL CONTROL AGENT, A POLYETHER-MODIFIED TRISILOXANE AND FUMED OR PRECIPITATED SILICA

CROSS-REFERENCE TO RELATED APPLICATION(S)

This application is a 35 U.S.C. § 371 national phase entry of PCT/EP2015/072346, filed on Sep. 29, 2015, which claims priority of European Patent Application No. 14187473.5, filed on Oct. 2, 2014, and European Patent Application No. 14194071.8, filed on Nov. 20, 2014, the contents of which are hereby incorporated by reference in their entirety.

BACKGROUND

Field of the Invention

The use of plant protection formulations comprising biological control agents (BCAs) has become a valuable alternative in the field of plant protection. Biological control agents directed against fungi or insects as well as those promoting plant health have been put on the market in different formulations.

Description of Related Art

The provision of suitable formulations for biological control agents nevertheless still pose a challenge due to the many factors contributing to the efficacy of the final formulation such as form of the biological control agent, temperature stability and shelf life as well as effect of the formulation in the application.

Suitable formulations are homogeneous and stable mixtures of active and inert ingredients which make the final product simpler, safer, and more efficacious to apply to a target. Commonly used additives in formulations include surfactants such as dispersants or wetting agents, solvents, emulsifiers, defoamers and stabilizers Commonly used formulations for biological control agents include WP, a solid formulation micronized to powder form and typically applied as suspended particles after dispersion in water, and WG, a formulation consisting of granules to be applied after disintegration and dispersion in water. The granules of a WG product has distinct particles within the range 0.2 to 4 mm. Water dispersible granules can be formed by agglomeration, spray drying, or extrusion techniques.

WP formulations are produced rather easily but they are dusty. Further, they are not easy to dose in the field. WG formulations are easier to handle for the user and in general have lower dust content than WP formulations.

An example for a liquid formulation is SC, a water-based suspension of solid active ingredient in a fluid usually intended for dilution with water before use. In such formulations, the active ingredient tends to settle over time and this is the reason why thickeners are used. Another liquid formulation type is EC, a solution of active ingredient combined with surfactants like e. g. emulsifying agents in a water insoluble organic solvent which will form an emulsion when added to water. Such formulation tends to be more hazardous to the operator and the environment due to the organic solvents used.

An enormous number of formulants have been utilized in experimental and commercial formulations of biological control agents (for a more detailed description and list see Schisler et al., Phytopathology, Vol 94, No. 11, 2004). Generally, formulants can be grouped as either carriers (fillers, extenders) or formulants that improve the chemical, physical, physiological or nutritional properties of the formulated biomass. A comparison of formulations and their effect on Trichoderma harzianum can be found in Küçük and Kivaniç (African Journal of Biotechnology 2005, Vol. 4 (5), pp. 483-486).

Another example for a formulation of a biological control agent is described in Tones et al., 2003, J Appl Microbiol, 94(2), pp: 330-9). However, it is clear that a formulation preserving a viability of the biological control agent, e. g. spores, of more than 70% for 4 months at 4 degrees C. only is not suitable for everyday use in the field. Rather, it is desirable that formulations of biological control agents have a sufficient shelf life even under conditions where cold storage is not possible.

SUMMARY

With the disadvantages described above there is still the need for a simple, easy to handle formulation recipe for biological control agents suitable both for foliar and soil application. Among other properties, such formulations shall ideally provide a good physical stability in the formulation concentrate, exhibit a suitable shelf life over time and ensure a superior distribution of the biological control agent both in spray and soil applications. Furthermore, the formulants shall preferably promote the biological efficacy of the BCA.

Accordingly, in one embodiment the present invention relates to a (liquid) composition comprising at least one biological control agent, wherein said biological control agent is spores of a spore forming fungus, a polyether-modified trisiloxane and fumed silica or precipitated silica, wherein said composition is essentially free of water.

As used herein "biological control" is defined as control of one or more pathogens or pests, in particular phytopathogenic micro-organisms, in the following also called phytopathogens, and/or insects and/or acarids and/or nematodes and/or mollusks and/or bacteria and/or rodents and/or weeds by the use of a second organism. Known mechanisms of biological control include endophytic bacteria and fungi that live in symbiosis with the plants and may cause a plant reaction toward pathogens, pests and stress or promote plant growth. Microorganisms can also act as biological control agents through their secondary metabolites. As an example, certain bacteria may control root rot by out-competing fungi for space or nutrients on the surface of the root. Active ingredients from bacteria, such as antibiotics, have been used to control pathogens. The active ingredients can be isolated and applied directly to the plant or the bacterial species may be administered so it produces the active ingredient in situ. Other means of exerting biological control include the application of certain fungi producing specific metabolites such as toxins, enzymes or plant hormones or attacking the target pest/pathogen directly. Again further means of biological control include the application of fungi or certain fungal spores to the soil where the funfus itself invased e.g. insect pathogens such as nematodes. "Biological control" as used in connection with the present invention may also encompass microorganisms having a beneficial effect on plant health, growth, vigor, stress response or yield.

The term "at least one" indicates that in any case one biological control agent is present in the formulation according to the invention. However, more than one such as (at least) two, (at least) three, (at least) four, (at least) 5 or even more biological control agents may be present in the formulation according to the invention.

Biological control agents as used in the present invention include fungal spores, i.e. sexually (e. g. oospores, zygospores or ascospores) and asexually (e. g. conidia and chlamydospores, but also uredospores, teleutospores and ustospores) formed spores. Preferably the spores are conidia.

If more than one biological control agent is present mixtures can be of the same kind, e. g. spores such as conidia of different fungal strains, or of different nature, such as a mixture of spores of one strain with conidia and/or chlamydospores of one or more other strains.

The composition further comprises a polyether-modified trisiloxane of formula I $$R^1-\underset{\underset{R^1}{|}}{\overset{\overset{R^1}{|}}{Si}}-O-\left[\underset{\underset{R^1}{|}}{\overset{\overset{R^1}{|}}{Si}}-O\right]_a-\left[\underset{\underset{R^1}{|}}{\overset{\overset{R^1}{|}}{Si}}-O\right]_b-\underset{\underset{R^1}{|}}{\overset{\overset{R^1}{|}}{Si}}-R^1 \qquad \text{Formula (I)}$$

where
$R^1$ represents independent from each other identical or different hydrocarbyl radicals having 1-8 carbon atoms, preferred methyl-, ethyl-, propyl- and phenyl radicals, particularly preferred are methyl radicals.
a=0 to 1, preferred 0 to 0.5, particularly preferred 0,
b=0.8 to 2, preferred 1 to 1.2, particularly preferred 1,
in which: a+b<4 and b>a, preferred a+b<3 and particularly preferred a+b<2.
$R^2$ represents independent from each other identical or different polyether radicals of general formula (II)

$$R^3O[CH_2CH_2O]_c[CH_2CH(CH_3)O]_d[CHR^4CHR^4O]_eR^5 \qquad \text{Formula (II)}$$

$R^3$=independent from each other identical or different, bivalent hydrocarbyl radicals having 2-8 carbon atoms, which are optionally interrupted by oxygen atoms, preferred rest is the general formula (III) wheri n=2-8, particularly preferred —$CH_2$—$CH_2$—$CH_2$—, $$-[CH_2]_n- \qquad \text{Formula (III)}$$

$R^4$=independent from each other identical or different hydrocarbyl radicals having 1-12 carbon atoms or hydrogen radical, preferably a methyl-, ethyl-, phenyl- or a hydrogen radical.
$R^5$=independent from each other identical or different hydrocarbyl radicals having 1-16 carbon atoms, which are optionally contain urethane functions, carbonyl functions or carboxylic acid ester functions, or hydrogen radical, preferred methyl or H, particularly preferred H.
C=0 to 40, preferred 1 to 15, particularly preferred 2 to 10
d=0 to 40, preferred 0 to 10, particularly preferred 1 to 5
e=0 to 40, preferred 0 to 5, particularly preferred 0,
in which c+d+e>3

The polyether-modified trisiloxanes described above can be prepared by methods well known to the practitioner by hydrosilylation reaction of a Si—H containing siloxane and unsaturated polyoxyalkylene derivatives, such as an allyl derivative, in the presence of a platinum catalyst. The reaction and the catalysts employed have been described for example, by W. Noll in "Chemie and Technologie der Silicone", $2^{nd}$ ed., Verlag Chemie, Weinheim (1968), by B. Marciniec in "Appl. Homogeneous Catal. Organomet. Compd. 1996, 1, 487). It is common knowledge that the hydrosilylation products of SiH-containing siloxanes with unsaturated polyoxyalkylene derivatives can contain excess unsaturated polyoxyalkylene derivative.

Examples of water soluble or self-emulsifyable polyether-modified (PE/PP or block-CoPo PEPP) trisiloxanes include but are not limited to those described by CAS-No 27306-78-1 (e.g. Silwet L77 from MOMENTIVE), CAS-No 134180-76-0 (e.g. BreakThru S233 or BreakThru S240 from Evonik), CAS-No 67674-67-3 (e.g Silwet 408 from WACKER), other BreakThru-types, and other Silwet-types.

Preferred polyether-modified trisiloxanes include those described by CAS-No 134180-76-0, in particular BreakThru S240. In one preferred embodiment, the polyether-modified trisiloxane has the chemical denomination oxirane, mono(3-(1,3,3,3-tetramethyl-1-((trimethylsilyl)oxy)disiloxanyl)propyl)ether.

A formulation according to the invention comprising a polyether-modified trisiloxane, in addition to the advantages described above, fulfills the requirement of reducing surface tension even in high dilutions, e. g. for soil applications, since such formulation contains a high concentration of polyether-modified trisiloxane being a surfactant. Furthermore, polyether-modified trisiloxanes are themselves already viscous so that normally no thickening agent is necessary. Accordingly, a formulation comprising a high concentration of polyether-modified trisiloxane and additionally fumed silica or precipitated silica would not be envisaged by the skilled artisan wishing to obtain a liquid composition comprising a biological control agent. In the present invention, fungal spores were found to survive in compositions essentially free of water. However, it was also found that they tend to sediment and such sediments can hardly or not at all be resuspended.

Fumed silica or precipitated silica is added to the present formulation in order to prevent (irreversible) sedimentation. It was found that such agent builds a network within the polyether-modified trisiloxane which prevents or at least severely reduces spore sedimentation and does not influence viability of the spores. Accordingly, fumed silica or precipitated silica provides long term stability when the formulation is at rest or in storage.

Silica (or silicon dioxide) is a chemical compound that is an oxide of silicon with the chemical formula $SiO_2$. It is most commonly found in nature as sand or quartz, as well as in the cell walls of diatoms. Silica is manufactured in several forms including fused quartz, crystal, fumed silica (or pyrogenic silica), colloidal silica, silica gel, and aerogel. Silica is a common additive in the production of foods, where it is used primarily as a flow agent in powdered foods, or to absorb water in hygroscopic applications. It is also known as the primary component of diatomaceous earth and of rice husk ash, which is used, for example, in filtration and cement manufacturing. Silica used as rheological control agents are derived from either natural or synthetic origin.

In connection with the present invention, said silica is fumed or precipitated silica.

Fumed silica, also known as pyrogenic silica, either hydrophilic or hydrophobic, usually is composed of amorphous silica fused into branched, chainlike, three-dimensional secondary particles which then agglomerate into tertiary particles. The resulting powder has an extremely low bulk density and high surface area. Both hydrophilic and hydrophobic fumed silica can be used in the present invention Fumed silica usually has a very strong thickening effect. The primary particle size is ca. 5-50 nm. The particles are non-porous and have a surface area of ca. 50-600 m$^2$/g.

Hydrophilic fumed silica is made from flame pyrolysis of silicon tetrachloride or from quartz sand vaporized in a 3000° C. electric arc. Major global producers are Evonik Industries, tradename AEROSIL®); Cabot Corporation, tradename Cab-O-Sil®; Wacker Chemie, HDK product range; and OCI, tradename Konasil®.

Hydrophilic fumed silica can be hydrophobized by further treatment with reactive silicium-containing agents in order to modify the physicochemical properties of the silica. Typically hydrophobisation takes place by treatment of a hydrophilic fumed silica with agents like hexaalkyldisilanes (e.g. $((CH_3)_3Si)_2$), trialkylsilylchlorides (e.g. $(CH_3)_3SiCl$) or dialkyldichlorsilanes (e.g. $(CH_3)_2SiCl_2$). Hydrophobized fumed silica is available e.g. from Evonik Industries (AEROSIL R-types), and Cabot (Cab-O-Sil).

Best results are obtained using a hydrophilic fumed silica having a BET surface area of 150 to 350 m$^2$/g, e. g. 150, 200, 250, 300 or 350.

Precipitated silica is produced by acidifying aqueous alkaline silicate solutions with mineral acids. Variations of the precipitation process lead to different precipitated silica qualities namely with different specific surface areas. The precipitates are washed and dried. Precipitated silica having a particle size of below 10 μm are most effective for the present invention. The specific surface area is typically from ca. 50-500 m$^2$/g. Global producers are for example Evonik Industries, tradename SIPERNAT® or Wessalon®; Rhodia, tradename Tixosil®; and PPG Industries, tradename Hi-Sil™.

In a preferred embodiment the silica concentration is between 0.1 to 9 wt.-%, e. g. of 3 to 7 or 4 to 6 wt.-%. In one preferred embodiment, e.g. where spores of Purpureocillium lilacinum (formerly known as Paecilomyces lilacinus) are used, the silica concentration is at least 5 wt.-%. Alternatively it may range between 5 and 7 wt.-%. In particular, the silica concentration may be at least 0.1 wt.-%, at least 0.2 wt.-%, at least 0.5 wt.-%, at least 1 wt.-%, at least 1.5 wt.-%, at least 2 wt.-%, at least 2.5 wt.-%, at least 3 wt.-%, at least 4 wt.-%, at least 4.5 wt.-% at least 5 wt.-%, at least 5.5 wt.-%, at least 6 wt.-%, at least 6.5 wt.-%, at least 7 wt.-%, at least 7.5 wt.-%, at least 8 wt.-%, at least 8.5 wt.-% or at least 9 wt.-% as well as any specific of the foregoing values and essentially depends on the physical properties of the biological control agent as well as those of the carrier. In general, the silica concentration in the formulation according to the invention may also depend on the biological control agent, e.g. on the size of the fungal spores. Bigger spores are believed to necessitate less silica in order to prevent sedimentation.

The formulation types described supra were mainly developed for agrochemicals and not for biological control agents where the requirements differ already due to the fact that such BCAs are living organisms in a dormant form. Furthermore, stability requirements for BCAs as compared to conventional agrochemicals are generally more demanding. Accordingly, formulations comprising a low concentration of water or even being essentially free of water are a preferred formulation type for BCAs. If water is present, such water mainly comes from water in the dried spore powder or traces of water in the other formulants. Accordingly, the water concentration highly depends on the amount of spore powder mixed into the composition of the invention. The higher the amount of spore powder the higher the water content may be. Water concentrations of between 0.3 wt.-% and 8 wt.-%, such as 0.3 wt.-% and 5 wt.-%, or between 4 wt.-% and 7 wt.-% are possible due to these facts, which range would then fall within the definition of "essentially free of water". The amount of spore powder in the composition according to the invention also depends on the application so that a composition for use in nematode control may need a higher spore concentration than one for use for increasing plant health in general. Accordingly, exemplary water concentrations include 1%, 2%, 3%, 4%, 5%, 6%, 7% and 8% which all fall within the definition of "essentially free of water". In other words, "essentially free of water" means a water content in the formulation according to the invention of 8% or less, preferably 7% or less, even more preferably 5% or less. This water content of 8 wt.-% or less of the formulation is also denominated "residual water". As indicated above, such residual water is comprised in the ingredients of the formulation of the invention which means that it is not added as a separate ingredient. Accordingly, the residual water content of the formulation of the invention is 8 wt.-% or less, such as any of the above values. Whereas the added percentages of fungal spores polyether-modified trisiloxane and fumed or precipitated silica shall not exceed 100%, the residual water content may be given in the formulation of the invention without adding up to the former ingredients due to said "residual water" being comprised in the other ingredients.

The water content of the spore powder prior to addition into the formulation according to the invention may be measured according to methods well-known in the art, e.g. using a moisture analyzer such as one available from Sartorius (Type MA 30). Using this moisture analyzer two samples of 4 g out of a spore preparation are taken. The moisture analyzer is adjusted to a temperature of 105° C. and 4 g of spore powder applied.

For soil applications a further prerequisite is that the biological control agent can be distributed well in the soil. For this, a significantly lower surface tension also in high dilution is desirable. This can be achieved by using surface-active additives such as tensides or surfactants. For such effect, high amounts/concentrations of such tensides such as silicon-based tensides are needed. In conventional formulations only relatively low percentages of sufactants are used which are not sufficient to lower the surface tension of formulations in high aqueous dilution. Furthermore, it was expected that the viability of microorganisms would be substantially lower if a surfactant is present. Another problem could be that even in the presence of viscous surfactants, the BCA tends to sediment irreversibly after a time and/or can only be resuspended with inapplicable time and effort so that the formulation would not be usable any further. In aqueous formulations sedimentation is inhibited by addition of rheological control agents of various types including clays and silicas. In the present invention, it was surprisingly found that some of such thickening agents are also effective in essentially water-free formulations according to the invention and essentially prevent sedimentation to provide a stable formulation of BCAs.

In another preferred embodiment the composition is formulated as a dispersible concentrate.

Suspending the biological control agent in a polyether-modified trisiloxane results in a dispersible concentrate (DC). For the purpose of the present invention and in the absence of an official denomination for the new formulation type of the present invention, it is called DC since this comes closest to its composition. The formulation according to the present invention is a dispersible concentrate wherein the term "dispersible" relates to dispersibility in water. The formulation of the present invention was found to penetrate the soil exceptionally well upon application.

In another more preferred embodiment the composition is essentially free of oil. In connection with the present invention, an oil shall be defined as any liquid which is essentially not water-miscible or self-emulsifyable in water, e.g. paraffinic oils, fatty acid triglycerides, fatty acid monoesters, certain silicone oils, aromatic solvents or other water-immiscible organic solvents, but not the polyether-modified trisiloxane used in the present invention. The term "essentially free of oil" refers to a content of oil of less than 5 wt.-%, preferably less than 4 wt.-%, even more preferably less than 3 wt.-% and most preferably less than 2 wt.-% such as 1 wt.-%, 0.1 wt.-%, 0.05 wt.-% or even 0.01 wt.-%. It cannot be excluded that the composition of the present invention contains traces of oil due to the production process of its ingredients. The formulation of the present invention does not contain oil except for such traces. Ingredients such as polyether-modified trisiloxane would normally be seen as an oil according to the above definition of oil (e. g. a silicone oil). However, it is understood that polyether-modified trisiloxane is explicitly not seen as oil within the meaning of the present invention.

In another preferred embodiment, the composition further comprises an antifoaming agent.

Surfactants such as polyether-modified trisiloxane may induce unwanted foaming which can be reduced or prevented by the addition of at least one antifoaming agent.

Suitable antifoaming agents are all agents which can customarily be employed in agrochemical agents for this purpose.

In another preferred embodiment, the composition is suitable for soil applications. Soil applications include drip irrigation or drench application as well as application by a micro sprinkler. In some cases, also an in-furrow application is envisaged.

In another preferred embodiment the biological control agent is a fungal microorganism that exhibits activity against insects (insecticide), acarids (acaricide), nematodes (nematicide), molluscs (molluscicide), bacteria (bactericide), rodents (rodenticide), weeds (herbicide) and/or phytopathogens (e. g. fungicide).

"Insecticides" as well as the term "insecticidal" refers to the ability of a substance to increase mortality or inhibit growth rate of insects. As used herein, the term "insects" includes all organisms in the class "Insecta". The term "pre-adult insects" refers to any form of an organism prior to the adult stage, including, for example, eggs, larvae, and nymphs.

"Acaricide" as well as the term "acaricidal" refer to the ability of a substance to increase mortality or inhibit growth rate of acarides, e.g. ticks and mites.

"Nematicides" and "nematicidal" refers to the ability of a substance to increase mortality or inhibit the growth rate of nematodes. In general, the term "nematode" comprises eggs, larvae, juvenile and mature forms of said organism.

Biological control agents active against phytopathogens such as phytopathogenic fungi are suitable to increase mortality or inhibit growth rate of phytopathogens such as phytopathogenic fungi or viruses.

Biological control agents active against molluscs are suitable to increase mortality or inhibit growth rate of molluscs such as snails and slugs.

Biological control agents active against rodents are suitable to increase mortality or inhibit growth rate of rodents.

Biological control agents active against weeds are suitable to increase mortality or inhibit growth rate of weeds.

In a preferred embodiment the composition further comprises at least one synthetic plant protective agent provided such synthetic plant protective agent does not adversely affect the activity of the biological control agent.

Synthetic plant protective agents in connection with the present invention include chemical fungicides, insecticides, bactericides, miticides, acaricides, molluscicides, rodenticides and herbicides as well as safeners and growth enhancing agents.

Chemical fungicides include those belonging to the class inhibitors of the ergosterol biosynthesis, inhibitors of the respiratory chain at complex I, II or III, inhibitors of the mitosis and cell division and compounds to have a multisite action, compounds capable to introduce a host defence, inhibitors of the amino acid and/or protein biosynthesis, inhibitors of the ATP production, inhibitors of the cell wall synthesis, inhibitors of the lipid and membrane synthesis, inhibitors of the melanine biosynthesis, inhibitors of the nucleic acid synthesis, inhibitors of the signal transduction, compounds capable to act as an uncoupler, and other fungicides.

Chemical insecticides include those belonging to the class of acetylcholinesterase (AChE) inhibitors, nicotinic acetylcholine receptor (nAChR) agonists, nicotinic acetylcholine receptor (nAChR) allosteric activators, nicotinic acetylcholine receptor (nAChR) channel blockers and ryanodine receptor modulators, GABA-gated chloride channel antagonists and chloride channel activators, sodium channel modulators/voltage-dependent sodium channel blockers and voltage-dependent sodium channel blockers, juvenile hormone mimics, miscellaneous non-specific (multi-site) inhibitors, selective homopteran feeding blockers, mite growth inhibitors, microbial disruptors of insect midgut membranes, inhibitors of mitochondrial ATP synthase, uncouplers of oxidative phoshorylation via disruption of the proton gradient, inhibitors of chitin biosynthesis (type 0), inhibitors of chitin biosynthesis (type 1), moulting disruptors, ecdysone receptor agonists, octopamine receptor agonists, mitochondrial complex III electron transport inhibitors, mitochondrial complex I electron transport inhibitors, inhibitors of acetyl CoA carboxylase, mitochondrial complex IV electron transport inhibitors, mitochondrial complex II electron transport inhibitors, and further insecticides In one embodiment, the fungal spores are conidia. Conidia are a kind of spores formed by fungi e.g. of the genus *Paecilomyces*. Conidia are asexually formed and include but are not limited to aleurispores, anellospores, arthrospores, phialospores and pynidiospores. Conidia are not intended to survive very harsh environmental conditions. Accordingly, it was even more surprising that conidia could survive in the composition of the present invention which is essentially free of water.

In another embodiment, the fungal spores are chlamydospores.

In one embodiment, the fungal spores are sexually formed. Sexually formed spores which can be used in the present invention include oospores, zygospores or ascospores.

In another more preferred embodiment said spores are dried spores.

Methods for preparing dried spores are well known in the art and include fluidized bed drying, spray drying, vacuum drying and lyophilization. Conidia may be dried in 2 steps:

For conidia produced by solid-state fermentation first the conidia covered culture substrate is dried before harvesting the conidia from the dried culture substrate thereby obtaining a pure conidia powder. Then the conidia powder is dried further using vacuum drying or lyophilization before formulating it according to the invention. For formulation, preferably, the polyether-modified trisiloxane and fumed silica or precipitated silica are combined in the desired ratio according to methods well-known in the art and provided e.g. in manufacturer's instructions, to form a carrier according to the invention. For example, such method of preparing a carrier includes applying high shear to disperse the fumed silica or precipitated silica in the polyether-modified trisiloxane to result in a homogenous mixture prior to mixing with the biological control agent and optionally further ingredients in the desired ratio. Preferably the polyether-modified trisiloxane is circulated from a receiving vessel via a rotor/stator machine, and the silica powder is introduced, using a feed device, into the shear zone between the slots in the rotor teeth and the stator slots, continuously or discontinuously, and with the rotor stator machine running, the feed device closes and shearing continues in such a way that the shear rate is in the range of between 1000 and 10000 s$^{-1}$. The process of introducing the silica powder into the polyether-modified trisiloxane is preferably carried out while reducing air intake, such as under application of vacuum, even more preferably high vacuum which reduces gas content.

In yet another preferred embodiment said fungal spores are present in the formulation according to the invention in a concentration of between at least about $1\times10^5$/ml and about $2\times10^{11}$/ml, such as $1\times10^6$/ml, $1\times10^7$/ml, $1\times10^8$/ml. Chlamydospores may be present in a concentration of between about $1\times10^6$/ml and about $1\times10^9$/ml. Accordingly, fungal spores may be present in a concentration of e.g. about $1\times10^7$/ml, $1\times10^8$/ml, $5\times10^8$/ml, $1\times10^9$/ml, $5\times10^9$/ml, $1\times10^{10}$/ml, $5\times10^{10}$/ml, $1\times10^{11}$/ml or $1.5\times10^{11}$/ml, all depending on the requirements of the application. Chlamydospores may be present in a concentration of e.g. about $5\times10^6$/ml, $1\times10^7$/ml, $5\times10^7$/ml, $1\times10^8$/ml or $5\times10^8$/ml, all depending on the requirements of the application.

Depending on the size of the spores used and the desired spore concentration in the composition, different amounts of spore powder need to be used. Exemplary percentages range from 0.5 wt.-% to 40 wt.-%, such as about 3 wt.-%, about 5 wt.-%, about 7 wt.-%, about 10 wt.-%, about 15 wt.-%, about 20 wt.-%, about 25 wt.-%, about 30 wt.-%, about 35 wt.-% or about 40 wt.-%.

If the at least one biological control agent has a fungicidal effect, it may be selected from B2.1 *Coniothyrium minitans*, in particular strain CON/M/ 91-8 (Accession No. DSM-9660; e.g. Contans® from Prophyta); B2.3 *Microsphaeropsis ochracea*, in particular strain P130A (ATCC deposit 74412); B2.5 *Trichoderma* spp., including *Trichoderma atroviride*, strain SC1 described in International Application No. PCT/IT2008/000196); B2.6 *Trichoderma harzianum rifai* strain KRL-AG2 (also known as strain T-22/ATCC 208479, e.g. PLANTSHIELD T-22G, Rootshield®, and TurfShield from BioWorks, US); B2.7 *Arthrobotrys dactyloides;* B2.8 *Arthrobotrys oligospora;* B2.9 *Arthrobotrys superba;* B2.10 *Aspergillus flavus*, e. g. strain NRRL 21882 (e.g. Afla-Guard® from Syngenta); B2.11 *Aspergillus flavus*, e. g. strain AF36 (e.g. AF36 from Arizona Cotton Research and Protection Council, US); B2.14 *Gliocladium roseum*, e. g. strain 321U from Adjuvants Plus; B2.15 *Phlebiopsis* (or *Phlebia* or *Peniophora*) *gigantea*, in particular strain VRA 1835 (ATCC 90304); B2.16 *Phlebiopsis* (or *Phlebia* or *Peniophora*) *gigantea*, in particular strain VRA 1984 (DSM16201); B2.17 *Phlebiopsis* (or *Phlebia* or *Peniophora*) *gigantea*, in particular strain VRA 1985 (DSM16202); B2.18 *Phlebiopsis* (or *Phlebia* or *Peniophora*) *gigantea*, in particular strain VRA 1986 (DSM16203); B2.19 *Phlebiopsis* (or *Phlebia* or *Peniophora*) *gigantea*, in particular strain FOC PG B20/5 (IMI390096); B2.20 *Phlebiopsis* (or *Phlebia* or *Peniophora*) *gigantea*, in particular strain FOC PG SP log6 (IMI390097); B2.21 *Phlebiopsis* (or *Phlebia* or *Peniophora*) *gigantea*, in particular strain FOC PG SP log5 (IMI390098); B2.22 *Phlebiopsis* (or *Phlebia* or *Peniophora*) *gigantea*, in particular strain FOC PG BU3 (IMI390099); B2.23 *Phlebiopsis* (or *Phlebia* or *Peniophora*) *gigantea*, in particular strain FOC PG BU4 (IMI390100); B2.24 *Phlebiopsis* (or *Phlebia* or *Peniophora*) *gigantea*, in particular strain FOC PG 410.3 (IMI390101); B2.25 *Phlebiopsis* (or *Phlebia* or *Peniophora*) *gigantea*, in particular strain FOC PG 97/1062/116/1.1 (IMI390102); B2.26 *Phlebiopsis* (or *Phlebia* or *Peniophora*) *gigantea*, in particular strain FOC PG B22/SP1287/3.1 (IMI390103); B2.27 *Phlebiopsis* (or *Phlebia* or *Peniophora*) *gigantea*, in particular strain FOC PG SH1 (IM1390104); B2.28 *Phlebiopsis* (or *Phlebia* or *Peniophora*) *gigantea*, in particular strain FOC PG B22/SP1190/3.2 (IMI390105) (B2.15 to B2.28: e.g. Rotstop® from Verdera and FIN, PG-Agromaster®, PG-Fungler®, PG-IBL®, PG-Poszwald®, and Rotex® from e-nema, DE); B2.29 *Pythium oligandrum*, strain DV74 or M1 (ATCC 38472; e.g. Polyversum from Biopreparty, CZ); B2.35 *Talaromyces flavus*, e. g. strain VII7b; B2.36 *Trichoderma asperellum*, e. g. strain ICC 012 from Isagro; B2.37 *Trichoderma asperellum*, strain SKT-1 (e.g. ECO-HOPE® from Kumiai Chemical Industry); B2.38 *Trichoderma atroviride*, e. g. strain CNCM 1-1237 (e.g. Esquive® WP from Agrauxine, FR); B2.39 *Trichoderma atroviride*, strain no. V08/002387; B2.40 *Trichoderma atroviride*, strain NMI no. V08/002388; B2.41 *Trichoderma atroviride*, strain NMI no. V08/002389; B2.42 *Trichoderma atroviride*, strain NMI no. V08/002390; B2.43 *Trichoderma atroviride*, strain LC52 (e.g. Tenet by Agrimm Technologies Limited); B2.44 *Trichoderma atroviride*, strain ATCC 20476 (IMI 206040); B2.45 *Trichoderma atroviride*, strain T11 (IMI352941/CECT20498); B2.46 *Trichoderma harmatum;* B2.47 *Trichoderma harzianum;* B2.48 *Trichoderma harzianum rifai* T39 (e.g. Trichodex® from Makhteshim, US); B2.49 *Trichoderma harzianum*, in particular, strain KD (e.g. Trichoplus from Biological Control Products, SA (acquired by Becker Underwood)); B2.50 *Trichoderma harzianum*, strain ITEM 908 (e.g. Trianum-P from Koppert); B2.51 *Trichoderma harzianum*, strain TH35 (e.g. Root-Pro by Mycontrol); B2.52 *Trichoderma virens* (also known as *Gliocladium virens*), in particular strain GL-21 (e.g. SoilGard 12G by Certis, US); B2.53 *Trichoderma viride*, e. g. strain TV1 (e.g. Trianum-P by Koppert); B2.54 *Ampelomyces quisqualis*, in particular strain AQ 10 (e.g. AQ 10® by IntrachemBio Italia); B2.62 *Chaetomium cupreum* (e.g. BIOKUPRUM™ by AgriLife); B2.63 *Chaetomium globosum* (e.g. Rivadiom by Rivale); B2.64 *Cladosporium cladosporioides*, e. g. strain H39 (by Stichting Dienst Landbouwkundig Onderzoek); B2.66 *Dactylaria candida;* B2.67 *Dilophosphora alopecuri* (e.g. Twist Fungus); B2.68 *Fusarium oxysporum*, strain Fo47 (e.g. Fusaclean by Natural Plant Protection); B2.69 *Gliocladium catenulatum* (Synonym: *Clonostachys rosea f. catenulate*), e. g. strain J1446 (e.g. Prestop® by AgBio Inc. and also e.g. Primastop® by Verdera Oy); B2.70 *Lecanicillium lecanii* (formerly known as *Verticillium lecanii*) *conidia*, e. g. of strain KV01 (e.g. Vertalec® by Koppert/Arysta); B2.71 *Penicillium vermiculatum;* B2.75 *Trichoderma atroviride*, strain SKT-1 (FERM P-16510); B2.76 *Trichoderma atroviride,* strain SKT-2 (FERM P-16511); B2.77 *Trichoderma atroviride,* strain SKT-3 (FERM P-17021); B2.78 *Trichoderma gamsii* (formerly *T. viride*), strain ICC080 (IMI CC 392151 CABI, e.g. BioDerma by AGROBIOSOL DE MEXICO, S.A. DE C.V.); B2.79 *Trichoderma harzianum,* strain DB 103 (e.g. T-Gro 7456 by Dagutat Biolab); B2.80 *Trichoderma polysporum,* strain IMI 206039 (e.g. Binab TF WP by BINAB Bio-Innovation AB, Sweden); B2.81 *Trichoderma stromaticum* (e.g. Tricovab by Ceplac, Brazil); B2.83 *Ulocladium oudemansii,* in particular strain HRU3 (e.g. Botry-Zen® by Botry-Zen Ltd, NZ); B2.84 *Verticillium albo-atrum* (formerly *V. dahliae*), strain WCS850 (CBS 276.92; e.g. Dutch Trig by Tree Care Innovations); B2.86 *Verticillium chlamydosporium;* B2.87 mixtures of *Trichoderma asperellum* strain ICC 012 and *Trichoderma gamsii* strain ICC 080 (product known as e.g. BIO-TAM™ from Bayer CropScience LP, US); and 2.88 *Simplicillium lanosoniveum.*

In a preferred embodiment, the biological control agent having fungicidal activity is selected from

*Coniothyrium minitans,* in particular strain CON/M/91-8 (Accession No. DSM-9660) (available as Contans® from Prophyta, DE); *Microsphaeropsis ochracea* strain P130A (ATCC 74412); *Aspergillus flavus,* strain NRRL 21882 (available as Afla-Guard® from Syngenta) and strain AF36 (available as AF36 from Arizona Cotton Research and Protection Council, US); *Gliocladium roseum,* strain 321U from Adjuvants Plus; *Phlebiopsis* (or *Phlebia* or *Peniophora*) *gigantea,* in particular the strains VRA 1835 (ATCC 90304), VRA 1984 (DSM16201), VRA 1985 (DSM16202), VRA 1986 (DSM16203), FOC PG B20/5 (IMI390096), FOC PG SP log6 IMI390097), FOC PG SP log5 (IMI390098), FOC PG BU3 (IMI390099), FOC PG BU4 (IMI390100), FOC PG 410.3 (IMI390101), FOC PG 97/1062/116/1.1 (IMI390102), FOC PG B22/SP1287/3.1 (IMI390103), FOC PG SH1 (IMI390104), FOC PG B22/SP1190/3.2 (IMI390105) (available as Rotstop® from Verdera and FIN, PG-Agromaster®, PG-Fungler®, PG-IBL®, PG-Poszwald®, and Rotex® from e-nema, DE); *Pythium oligandrum,* strain DV74 or M1 (ATCC 38472) (available as Polyversum from Biopreparty, CZ); *Scleroderma citrinum; Talaromyces flavus,* strain VII7b; *Ampelomyces quisqualis,* in particular strain AQ 10 (available as AQ 10® by IntrachemBio Italia); *Gliocladium catenulatum* (Synonym: *Clonostachys rosea f. catenulate*) strain J1446 (available as Prestop® by AgBio Inc. and also available as Primastop® by Verdera Oy) and *Cladosporium cladosporioides,* e. g. strain H39 (by Stichting Dienst Landbouwkundig Onderzoek).

In an even more preferred embodiment, the biological control agent having fungicidal activity is selected from *Coniothyrium minitans,* in particular strain CON/M/91-8 (Accession No. DSM-9660) (available as Contans® from Prophyta, DE); *Talaromyces flavus,* strain VII7b; *Cladosporium cladosporioides,* e. g. strain H39 (by Stichting Dienst Landbouwkundig Onderzoek); and *Simplicillium lanosoniveum.*

If the at least one biological control agent has an insecticidal effect, it may be selected from C2.3 *Beauveria bassiana,* e. g. strain ATCC 74040 (e.g. Naturalis® from Intrachem Bio Italia); C2.4 *Beauveria bassiana* strain GHA (Accession No. ATCC74250; e.g. BotaniGuard Es and Mycontrol-O from Laverlam International Corporation); C2.5 *Beauveria bassiana* strain ATP02 (Accession No. DSM 24665); C2.6 *Beauveria bassiana* strain CG 716 (e.g. BoveMax® from Novozymes); C2.7 *Hirsutella citriformis;* C2.8 *Hirsutella thompsonii* (with some strains e.g. Mycohit and ABTEC from Agro Bio-tech Research Centre, IN); C2.9 *Lecanicillium lecanii* (formerly known as *Verticillium lecanii*), in particular conidia of strain KV01 (e.g. Mycotal® and Vertalec® from Koppert/Arysta); C2.10 *Lecanicillium lecanii* (formerly known as *Verticillium lecanii*) conidia of strain strain DAOM198499; C2.11 *Lecanicillium lecanii* (formerly known as *Verticillium lecanii*) conidia of strain strain DAOM216596; C2.12 *Lecanicillium muscarium* (formerly *Verticillium lecanii*), in particular strain VE 6/CABI(=IMI) 268317/CBS102071/ARSEF5128; C2.13 *Metarhizium anisopliae,* in particular strain F52 (DSM3884/ATCC 90448; e.g. BIO 1020 by Bayer CropScience and also e.g. Met52 by Novozymes); C2.14 *M. anisopliae* var *acridum* (e.g. GreenGuard by Becker Underwood, US); C2.15 *M. anisopliae* var *acridum* isolate IMI 330189 (ARSEF7486; e.g. Green Muscle by Biological Control Products); C2.16 *Nomuraea rileyi;* C2.17 *Paecilomyces fumosoroseus* (new: *Isaria fumosorosea*), in particular strain apopka 97 (e.g. PreFeRal® WG from Biobest); C2.18 *Paecilomyces fumosoroseus* (new: *Isaria fumosorosea*) strain FE 9901 (e.g. NoFly® from Natural Industries Inc., a Novozymes company); C2.19 *Aschersonia aleyrodis;* C2.20 *Beauveria brongniartii* (e.g. Beaupro from Andermatt Biocontrol AG); C2.24 *Metarhizium flavoviride;* and C2.25 *Mucor haemelis* (e.g. BioAvard from Indore Biotech Inputs & Research).

In a more preferred embodiment, fungal strains having an insecticidal effect may be selected from Beauveria bassiana, strain ATCC 74040 (available as Naturalis® from Intrachem Bio Italia), strain GHA (Accession No. ATCC74250) (available as BotaniGuard Es and Mycontrol-O from Laverlam International Corporation), strain ATP02 (Accession No. DSM 24665), strain CG 716 (available as BoveMax® from Novozymes); Hirsutella citriformis; Hirsutella thompsonii (with some strains available as Mycohit and ABTEC from Agro Bio-tech Research Centre, IN); Lecanicillium lecanii (formerly known as Verticillium lecanii) conidia of strain KV01 (available as Mycotal® and Vertalec® from Koppert/Arysta); Lecanicillium lecanii (formerly known as Verticillium lecanii) conidia of strain strain DAOM198499; Lecanicillium lecanii (formerly known as Verticillium lecanii) conidia of strain DAOM216596; Lecanicillium muscarium (formerly Verticillium lecanii), strain VE 6/CABI(=IMI) 268317/CBS102071/ARSEF5128; Metarhizium anisopliae, strain F52 (DSM3884/ATCC 90448) (available as BIO 1020 by Bayer CropScience and also available as Met52 by Novozymes); M. anisopliae var acridum (available as GreenGuard by Becker Underwood, US); M. anisopliae var acridum isolate IMI 330189 (ARSEF7486) (available as Green Muscle by Biological Control Products); Nomuraea rileyi; Paecilomyces fumosoroseus (new: Isaria fumosorosea), strain apopka 97 (available as PreFeRal® WG from Biobest); Paecilomyces fumosoroseus (new: Isaria fumosorosea) strain FE 9901 (available as NoFly® from Natural Industries Inc., a Novozymes company); and Beauveria brongniartii (e.g. Beaupro from Andermatt Biocontrol AG).

In an even more preferred embodiment, fungal strains having an insecticidal effect are selected from Beauveria bassiana, in particular strain ATCC 74040 (available as Naturalis® from Intrachem Bio Italia), strain GHA (Accession No. ATCC74250) (available as BotaniGuard Es and Mycontrol-O from Laverlam International Corporation), strain ATP02 (Accession No. DSM 24665), strain CG 716 (available as BoveMax® from Novozymes); Paecilomyces fumosoroseus (new: Isaria fumosorosea), strain apopka 97

(available as PreFeRal® WG from Biobest) and strain FE 9901 (e.g. NoFly® from Natural Industries Inc., a Novozymes company); Lecanicillium lecanii (formerly known as Verticillium lecanii), conidia of strain KV01 (available as Mycotal® and Vertalec® from Koppert/ Arysta), conidia of strain strain DAOM198499 or conidia of strain DAOM216596; Metarhizium anisopliae, strain F52 (DSM3884/ATCC 90448) (available as BIO 1020 by Bayer CropScience and also available as Met52 by Novozymes); Nomuraea rileyi; Lecanicillium muscarium (formerly Verticillium lecanii), strain VE 6/CABI(=IMI) 268317/CBS102071/ARSEF5128; and *Beauveria brongniartii* (e.g. Beaupro from Andermatt Biocontrol AG).

If the at least one biological control agent has a nematicidal effect, it may be selected from D2.3 *Paecilomyces lilacinus*, in particular spores of *P. lilacinus* strain 251 (AGAL 89/030550; e.g. BioAct from Prophyta); D2.4 *Trichoderma koningii*; D2.5 *Harposporium anguillullae*; D2.6 *Hirsutella minnesotensis*; D2.7 *Monacrosporium cionopagum*; D2.8 *Monacrosporium psychrophilum*; D2.9 *Myrothecium verrucaria*, strain AARC-0255 (e.g. DiTera™ by Valent Biosciences); D2.10 *Paecilomyces lilacinus*, in particular spores of *P. lilacinus* strain 251 (AGAL 89/030550) (available as BioAct from Prophyta); D2.11 *Paecilomyces variotii*, strain Q-09 (e.g. Nemaquim® from Quimia, MX); D2.13 *Stagonospora phaseoli* (e.g. from Syngenta); D2.14 *Trichoderma lignorum*, in particular strain TL-0601 (e.g. Mycotric from Futureco Bioscience, ES); D2.15 *Fusarium solani*, strain Fs5; D2.16 *Hirsutella rhossiliensis*; D2.17 *Monacrosporium drechsleri*; D2.18 *Monacrosporium gephyropagum*; D2.19 *Nematoctonus geogenius*; D2.20 *Nematoctonus leiosporus*; D2.22 *Paraglomus* sp, in particular *P. Brasilianum*; D2.23 *Pochonia chlamydosporia* (also known as *Vercillium chlamydosporium*), in particular var. *catenulata* (IMI SD 187; e.g. KlamiC from The National Center of Animal and Plant Health (CENSA), CU); D2.24 *Stagonospora heteroderae*; D2.25 *Meristacrum asterospermum*; and D2.27 *Duddingtonia flagrans*.

In a more preferred embodiment, fungal strains with nematicidal effect are selected from

*Paecilomyces lilacinus*, in particular spores of *P. lilacinus* strain 251 (AGAL 89/030550) (available as BioAct from Prophyta); *Harposporium anguillullae*; *Hirsutella minnesotensis*; *Monacrosporium cionopagum*; *Monacrosporium psychrophilum*; *Myrothecium verrucaria*, strain AARC-0255 (available as DiTera™ by Valent Biosciences); and *Paecilomyces variotii*; *Stagonospora phaseoli* (commercially available from Syngenta).

In an even more preferred embodiment, fungal strains with nematicidal effect are selected from *Paecilomyces lilacinus*, in particular spores of *P. lilacinus* strain 251 (AGAL 89/030550) (available as BioAct from Prophyta); and *Duddingtonia flagrans*.

If the at least one biological control agent supportsand/or promotes and/or stimulates plant health and plant growth it may be selected from E2.1 *Talaromyces flavus*, in particular strain VII7b; E2.2 *Trichoderma atroviride*, e. g. strain no. V08/002387; E2.3 *Trichoderma atroviride*, strain no. NMI No. V08/002388; E2.4 *Trichoderma atroviride*, strain no. NMI No. V08/002389; E2.5 *Trichoderma atroviride*, strain no. NMI No. V08/002390; E2.6 *Trichoderma harzianum*, strain ITEM 908 (e.g. Trianum-P from Koppert); E2.7 *Myrothecium verrucaria*, strain AARC-0255 (e.g. DiTera™ from Valent Biosciences); E2.8 *Penicillium bilaii*, strain ATCC 22348 (e.g. JumpStart® from Novozymes); E2.11 *Pythium oligandrum*, strain DV74 or M1 (ATCC 38472; e.g. Polyversum from Biopreprary, CZ); E2.14 *Trichoderma atroviride*, strain LC52 (e.g. Sentinel from Agrimm Technologies Limited); E2.15 *Trichoderma harzianum*, strain TSTh20; E2.16 *Trichoderma koningii*; E2.31 *Trichoderma harzianum*, strain KD (e.g. Eco-T from Plant Health Products, SZ); E2.32 *Trichoderma harzianum*, strain 1295-22; E2.33 *Trichoderma vixens*, strain GL-21; E2.34 *Verticillium alboatrum* (formerly *V. dahliae*), strain WCS850 (CBS 276.92; e.g. Dutch Trig from Tree Care Innovations); and E2.35 *Trichoderma atroviride*, strain LC52 (e.g. Tenet from Agrimm Technologies Limited).

In a more preferred embodiment, fungal strains having a beneficial effect on plant health and/or growth are selected from

*Talaromyces flavus*, strain VII7b; *Myrothecium verrucaria*, strain AARC-0255 (available as DiTera™ from Valent Biosciences); *Penicillium bilaii*, strain ATCC 22348 (available as JumpStart® from Novozymes); *Penicillium bilaii*, in particular strain ATCC 22348 (available as PB-50 PROVIDE from Philom Bios Inc., Saskatoon, Saskatchewan); and *Pythium oligandrum*, strain DV74 or M1 (ATCC 38472) (available as Polyversum from Biopreprary, CZ).

In an even more preferred embodiment, fungal strains having a beneficial effect on plant health and/or growth are selected from *Penicillium bilaii*, in particular strain ATCC 22348 (available as JumpStart® from Novozymes) and strain ATCC 22348 (available as PB-50 PROVIDE from Philom Bios Inc., Saskatoon, Saskatchewan).

If the at least one biological control agent has a herbicidal effect it may be selected from F2.1 *Phoma macrostroma*, strain 94-44B (e.g. Phoma H and Phoma P by Scotts, US); F2.3 *Colletotrichum gloeosporioides*, strain ATCC 20358 (e.g. Collego (also known as LockDown) by Agricultural Research Initiatives); and F2.4 *Stagonospora atriplicis*.

In a preferred embodiment the amount of polyether-modified trisiloxane ranges between 50 and 96% wt, such as between 70 and 90% wt or between 75 and 85% wt. Accordingly, the composition according to the present invention may comprise 50, 55, 60, 65, 70, 75, 80, 85, 90 or 95% wt polyether-modified trisiloxan and any value in between such as 71, 72, 73, 74, 76, 77, 78, 79, 81, 82, 83, 84, 86, 87, 88 and 89% wt.

In one embodiment, the composition according to the invention consists of only fungal spores, polyether-modified trisiloxane and fumed silica or precipitated silica, except for the mentioned traces of water and oil.

In a more preferred embodiment, said biological control agent is Paecilomyces lilacinus (recently re-classified as Purpureocillium lilacinum). A number of Paecilomyces lilacinus strains have been described for use as a biological control agent. Such strains include strain 251 in the products BioAct, MeloCon and NemOut produced by Prophyta GmbH (now Bayer CropScience Biologics GmbH), a strain 580 in the product Biostat WP (ATCC no. 38740) produced by Laverlam, a strain in the product Bio-Nematon produced by the company T. Stanes and Company Ltd., a strain in the product Mysis produced by the company Varsha Bioscience and Technology India Pvt Ltd., one in the product Bioiconema available from Nico Orgo Maures, India, one in the product Nemat, available from Ballagro Agro Tecnologia Ltda, Brazil and one in the product Spectrum Pae L available from Promotora Tecnica Industrial, S.A. DE C.V., Mexico.

In an even more preferred embodiment said Paecilomyces lilacinus is Paecilomyces lilacinus strain 251 as described in WO1991/002051 or a mutant thereof having all identifying characteristics of the respective strain.

Preferred spore concentrations in a formulation according to the invention for nematode control using Paecilomyces lilacinus, in particular P. lilacinus strain 251, range between $5 \times 10^9$ and $1 \times 10^{11}$ spores/ml, such as between $4.5 \times 10^{10}$ and $6 \times 10^{10}$, preferably at least $4 \times 10^{10}$, more preferably at least $5 \times 10^{10}$ spores/ml. Such formulation may comprise between 5 and 25 wt.-% spore powder, preferably between 10 wt.-% and 22 wt.-%, more preferably between 15 wt.-% and 21 wt.-% such as 16 wt.-%, 17 wt.-%, 18 wt.-%, 19 wt.-%, or 20 wt.-%. It is further preferred that in a formulation with Paecilomyces lilacinus, in particular P. lilacinus strain 251, as biological control agent, the concentration of fumed silica or precipitated silica ranges between 3.5 and 6% wt, such as between 4 and 5.5% wt, e.g. 4.4, 4.6, 4.8, 5.0 or 5.2% wt.

Such formulation with Paecilomyces lilacinus for nematode control, in particular P. lilacinus strain 251, as biological control agent, preferably contains between 0.5 and 3% wt water, preferably between 1 and 3%.

It is further preferred that in such formulation with Paecilomyces lilacinus, in particular P. lilacinus strain 251, as biological control agent, the concentration of polyether-modified trisiloxane ranges between 70 and 85% wt, preferably between 70 and 80% wt, such as between 73 and 78% wt, e.g. 74% wt, 75% wt, 76% wt or 77% wt or any value in between.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. cannabis), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana;* and in each case genetically modified types of these plants.

In another embodiment, the present invention discloses a method of producing a liquid composition according to the invention, comprising the steps of providing a carrier comprising a polyether-modified trisiloxane and fumed silica or precipitated silica in a concentration that in the final composition results in a concentration of between 50 and 96 wt.-% polyether-modified trisiloxane and between about 0.1 and 9 wt.-% fumed silica or precipitated silica agent, and incorporating a biological control agent into said carrier, wherein said biological control agent is spores of a spore forming fungus and wherein the composition is essentially free of water.

The fungal microorganism acting as biological control agent or producing the metabolite acting a biological control agent is cultivated according to methods known in the art or as described elsewhere in this application on an appropriate substrate, e. g. by submerged fermentation or solid-state fermentation, e. g. using a device disclosed in WO2005/012478 or WO1999/057239. Subsequently, the microorganism or its organs used as biological control agent is/are separated from the substrate. The substrate populated with the microorganism is dried preferably before the separation step. The microorganism or its organs may be dried via e. g. freeze-drying, vacuum drying or spray drying after separation. After separation and drying, the microorganism or its organs is/are suspended in the carrier according to the invention comprising fumed silica or precipitated silica and a polyether-modified trisiloxane as described herein in order to form the formulation according to the invention.

In one embodiment, after cultivation and prior to the separation step, the culture substrate is treated with an appropriate dispersion method. Alternatively, in another embodiment, after the drying step the culture is treated by an appropriate grinding method. In this case, separation takes place after the treatment step through methods known in the art such as sieving, filtration, air classifying, decantation- or centrifugation methods.

The amount of the formulation according to the invention when brought to the field, i.e. after dispersal in water, is at least 0.05 l/ha (hectare), such as 0.05 to 3 l/ha, 0.5 to 1.5 l/ha, such as 0.1, 0.2, 0.3, 0.4, 0.5, 0.6, 0.7, 0.75, 0.8, 0.9, 1.0, 1.1, 1.2, 1.3, 1.4 or 1.5 l/ha. In one embodiment where the formulation comprises Paecilomyces lilacinus spores for nematode control, the amount to the field preferably ranges between 0.3 and 0.9 h/ha.

In a further embodiment, the present invention relates to a method for controlling phytopathogenic fungi, insects and/or nematodes in or on a plant, for enhancing growth of a plant or for increasing plant yield or root health comprising applying the liquid composition according to the invention to said plant or to a plot where plants are growing or are to be grown.

In another embodiment the present invention relates to the use of a composition according to the invention for controlling phytopathogenic fungi, insects and/or nematodes in, on and/or around a plant, for enhancing growth of a plant or for increasing plant yield or root health.

The examples further illustrate the invention in a non-limiting fashion.

EXAMPLE 1

Synthesis of Polyether-Modified Siloxane Surfactant within the Scope of the Invention Firstly, 198 g of a polyether of the general formula $$CH_2{=}CHCH_2O[CH_2CH_2O]_{12}Me$$

were placed in a 500 ml three-necked flask with stirrer and reflux condenser and heated to 90° C. 10 ppm of Pt in form of the Karstedt catalyst were added and the mixture was stirred for 10 minutes. After this 52 g of 1,1,1,3,5,5,5-

Heptamethyltrisiloxane were added dropwise within 15 minutes under constant stirring. An exothermic reaction was observed. Finally, the mixture was stirred for 4 h at 90° C.

EXAMPLE 2

Evaluation of Sedimentation Rate of Compositions Comprising Mixtures of a Polyether-Modified Trisiloxane and Fumed Silica and Conidia of Purpureocillium Lilacinum A test was carried out using a pure polyether-modified trisiloxane as negative control and 3 mixtures of polyether-modified trisiloxane with fumed silica. To create the mixtures the following ratios of polyether-modified trisiloxane (BreakThru S 240) and fumed silica (Aerosil 200) have been used: 97.5:2.5, 95.0:5.0, 92.5:7.5. Aerosil 200 was mixed into BreakThru S 240 applying an Ultra Turax for 10 min at 10,000 rpm and for further 5 min at 5600 rpm. The four liquids then where mixed with Purpureocillium lilacinum conidia powder in a way that 20.25 g conidia powder (about $7 \times 10^{12}$ spores/g) were blended into 99.75 grams each liquid using an Ultra Turrax for 2 min at 5400 rpm. The resulting conidia suspensions contained $5.57 \times 10^{10}$ viable conidia per gram. The conidia suspensions then were filled into 20 ml glass bottles up to 1.5 cm below the top sealed and incubated at 54° C. to evaluate the influence of the mixtures on conidia sedimentation.

The sedimentation of the conidia on the bottom of the flasks where evaluated after 31 days by determining the height of the clear supernatant on top of the dark brown conidia suspension/sediment in percent of the complete height (see table 1 below).

TABLE 1

Height of the clear supernatant on top of the conidia sediment after incubation of different conidia formulation at 54° C. using a pure polyether-modified trisiloxane or mixtures of polyether-modified trisiloxane with fumed silica in different ratios.

| Incubation time | Height of the supernatant at ratio of BreakThru S 240 and Aerosil 200 in the test mixture (in %) | | | |
|---|---|---|---|---|
| at 54° C. | 100:0 | 97.5:2.5 | 95.0:5.0 | 92.5:7.5 |
| 31 days | 78.1 | 68.8 | 0.0 | 0.0 |

The results clearly indicate that, for Purpureocillium lilacinum conidia, a content of fumed silica of about 5% or higher homogenously mixed into a polyether-modified trisiloxane prevents the conidia from settling down.

EXAMPLE 3

Viability of Conidia in Formulations Comprising Polyether-Modified Trisiloxane and Fumed Silica as Compared to One Only Comprising Polyether-Modified Trisiloxane Four liquids comprising polyether-modified trisiloxane without (negative control) and with different amounts of fumed silica were prepared as described in Example 1, filled into 20 ml glass bottles up to 1.5 cm below the top, sealed and incubated at 30° C. to evaluate the influence of the mixtures on the conidia viability (see table 2 below).

TABLE 2

Viability of the conidia of *Purpureocillium lilacinum* in BreakThru S 240 and BreakThru S 240 blended with Aerosil 200 at 30° C.

| Used liquid conidia carrier | Ratio of blending | Conidia viability in % after incubation at 30° C. after | | | | | | | |
|---|---|---|---|---|---|---|---|---|---|
| | | 2 weeks | 4 weeks | 6 weeks | 8 weeks | 10 weeks | 12 weeks | 16 weeks | 21 weeks |
| BreakThru S 240 | n.a. | 83.30 | 84.23 | 77.78 | 78.99 | 76.90 | 78.64 | 64.62 | 50.62 |
| BreakThru S 240 blended with Aerosil 200 | 97.5:2.0 | 86.30 | 86.32 | 81.25 | 81.14 | 80.28 | 76.02 | 74.44 | 66.78 |
| BreakThru S 240 blended with Aerosil 200 | 95.0:5.0 | 88.31 | 86.88 | 85.43 | 84.84 | 80.69 | 78.93 | 62.32 | 55.78 |
| BreakThru S 240 blended with Aerosil 200 | 92.5:7.5 | 90.61 | 88.61 | 84.60 | 82.89 | 81.22 | 80.68 | 71.87 | 47.83 |

The viability of the conidia has not been significantly negatively affected by the addition of the fumed silica Aerosil 200.

EXAMPLE 4

Detailed Evaluation of Sedimentation Rate of Compositions Comprising Mixtures of a Polyether-Modified Trisiloxane and Fumed Silica and Conidia of Purpureocillium Lilacinum A test was carried out using a pure polyether-modified trisiloxane as negative control and 7 mixtures of polyether-modified trisiloxane with fumed silica. To create the mixtures the following ratios of polyether-modified trisiloxane (BreakThru S 240) and fumed silica (Aerosil 200) have been used: 93.5:6.5, 94.0:6.0, 94.5:5.5, 95.0:5.0, 95.5:4.5, 96.0:4.0. Aerosil 200 was mixed into the BreakThru S 240 applying an Ultra Turax for 10 min at 10,000 rpm and for further 5 min at 5600 rpm. The 8 resulting liquids then where mixed with Purpureocillium lilacinum conidia powder in a way that 20.23 g (containing about $7 \times 10^{12}$ spores/g) conidia powder were blended into 99.77 grams of each liquid using an Ultra Turax for 2 min at 5400 rpm. The resulting conidia suspensions contained $5.56 \times 10^{10}$ viable conidia per gram. The conidia suspensions then were filled into 20 ml glass bottles up to 1.5 cm below the top, sealed and incubated at 30 and 54° C. to evaluate the influence of the mixtures on conidia sedimentation.

Sedimentation of the conidia on the bottom of the flasks where evaluated after 14 and 30 days by determination of the height of the clear supernatant on top of the dark brown conidia suspension/sediment in percent of the complete height (see tables 3 and 4 below).

TABLE 3

Height of the clear supernatant on top of the conidia sediment after incubation of different conidia formulation at 54° C. using a pure polyether-modified trisiloxane or mixtures of polyether-modified trisiloxane with fumed silica in different ratios.

| Incubation time at 54° C. | Height of the supernatant at ratio of BreakThru S 240 and Aerosil 200 in the test mixture (in %) | | | | | | | |
|---|---|---|---|---|---|---|---|---|
| | 100:0 | 96.5:3.5 | 96.0:4.0 | 95.5:4.5 | 95.0:5.0 | 94.5:5.5 | 94.0:6.0 | 96.5:3.5 |
| 14 days | 40.6 | 18.8 | 9.4 | 4.7 | 1.6 | 0.0 | 0.0 | 0.0 |
| 30 days | 71.9 | 31.3 | 14.1 | 6.3 | 1.6 | 0.0 | 0.0 | 0.0 |

TABLE 4

Height of the clear supernatant on top of the conidia sediment after incubation of different conidia formulation at 30° C. using a pure polyether-modified trisiloxane or mixtures of polyether-modified trisiloxane with fumed silica in different ratios.

| Incubation time at 30° C. | Height of the supernatant at ratio of BreakThru S 240 and Aerosil 200 in the test mixture (in %) | | | | | | | |
|---|---|---|---|---|---|---|---|---|
| | 100:0 | 96.5:3.5 | 96.0:4.0 | 95.5:4.5 | 95.0:5.0 | 94.5:5.5 | 94.0:6.0 | 96.5:3.5 |
| 14 days | 18.8 | 9.4 | 4.7 | 3.1 | 1.6 | 0.6 | 0.0 | 0.0 |
| 30 days | 28.1 | 9.4 | 5.3 | 4.7 | 2.2 | 0.6 | 0.0 | 0.0 |

The results clearly indicate that, for conidia of Purpureocillium lilacinum, a content of fumed silica of about 5% or higher homogenously mixed into a polyether-modified trisiloxane prevents the conidia from settling down.

EXAMPLE 5

More Detailed Evaluation of Viability of Conidia in Formulations Comprising Polyether-Modified Trisiloxane and Fumed Silica as Compared to One Only Comprising Polyether-Modified Trisiloxane Eight liquids comprising polyether-modified trisiloxane without (negative control) and with different amounts of fumed silica were prepared as described in Example 3, filled into 20 ml glass bottles up to 1.5 cm below the top, sealed and incubated at 30° C. to evaluate the influence of the mixtures on conidia viability (see table 5 below).

TABLE 5

Viability of the conidia of *Purpureocillium lilacinum* in BreakThru S 240 and BreakThru S 240 blended with Aerosil 200 at 30° C.

| Used liquid conidia carrier | Ratio of blending | Conidia viability in % after incubation at 30° C. after | | | | | | | |
|---|---|---|---|---|---|---|---|---|---|
| | | 1 weeks | 2 weeks | 4 weeks | 6 weeks | 8 weeks | 10 weeks | 12 weeks | 17 weeks |
| BreakThru S 240 | n.a. | 94.63 | 82.68 | 83.15 | 71.36 | 69.28 | 69.69 | 61.43 | 63.05 |
| BreakThru S 240 blended with Aerosil 200 | 96.5:3.5 | 94.35 | 83.70 | 84.31 | 81.58 | 71.80 | 70.65 | 68.34 | 32.55* |
| BreakThru S 240 blended with Aerosil 200 | 96.0:4.0 | 93.43 | 83.57 | 85.84 | 76.70 | 70.98 | 69.06 | 64.39 | 62.84 |
| BreakThru S 240 blended with Aerosil 200 | 95.5:4.5 | 93.92 | 83.22 | 86.74 | 78.08 | 71.88 | 69.60 | 64.44 | 50.56 |

TABLE 5-continued

Viability of the conidia of *Purpureocillium lilacinum* in BreakThru
S 240 and BreakThru S 240 blended with Aerosil 200 at 30° C.

| Used liquid conidia carrier | Ratio of blending | Conidia viability in % after incubation at 30° C. after | | | | | | | |
|---|---|---|---|---|---|---|---|---|---|
| | | 1 weeks | 2 weeks | 4 weeks | 6 weeks | 8 weeks | 10 weeks | 12 weeks | 17 weeks |
| BreakThru S 240 blended with Aerosil 200 | 95.0:5.0 | 93.26 | 83.51 | 84.18 | 79.40 | 69.69 | 72.22 | 68.57 | 34.11* |
| BreakThru S 240 blended with Aerosil 200 | 94.5:5.5 | 93.41 | 84.46 | 85.34 | 77.23 | 71.96 | 70.65 | 72.62 | 33.33* |
| BreakThru S 240 blended with Aerosil 200 | 94.0:6.0 | 94.84 | 84.69 | 86.27 | 77.00 | 72.52 | 69.29 | 71.06 | 35.00* |
| BreakThru S 240 blended with Aerosil 200 | 96.5:3.5 | 94.28 | 84.16 | 85.11 | 75.95 | 71.53 | 72.35 | 70.58 | 53.90 |

*most likely experimental error, due to surplus of oxygen

The viability of the conidia has not been negatively affected by the addition of the fumed silica Aerosil 200.

EXAMPLE 6

Evaluation whether or not Dried Conidia of Cladosporium Cladosporioides Suspended in a Liquid Comprising a Mixture of a 95% Polyether-Modified Trisiloxane and and 6% Fumed Silica are Undergoing Sedimentation with Time A test was carried out using a mixture of polyether-modified trisiloxane with fumed silica. To create the mixtures a fumed silica (Aerosil 200) was mixed into a polyether-modified trisiloxane (BreakThru S 240) at a ratio of 6:94 applying an Ultra Turax for 10 min at 10,000 rpm and for further 5 min at 5600 rpm. The resulting liquid then was mixed with Cladosporium cladosporioides conidia powder in a way that 16 g conidia powder (about $8 \times 10^{11}$ conidia) were blended into 100 grams of the liquid using an Ultra Turax for 2 min at 5400 rpm. The resulting conidia suspensions contained $5.5 \times 10^9$ viable conidia per gram. The conidia suspensions then were filled into 20 ml glass bottles up to 1.5 cm below the top, sealed and incubated for at 50° C. to evaluate the influence of the mixtures on conidia sedimentation.

After an incubation time of 30 days no sedimentation of the conidia could be observed. There was no clear supernatant on top of the dark grey conidia suspension/sediment detectable.

EXAMPLE 7

Efficacy of the Composition according to the Invention Comprising Spores of Paecilomyces Lilacinus in Comparison with a WP Formulation of Paecilomyces Lilacinus Efficacy against root knot nematodes (*Meloidogyne incognita*) of a WG formulation dispersed in water and the formulation according to the invention both comprising equivalent spore concentrations of Paecilomyces lilacinus was compared in bell pepper, tomato, cucumber and lettuce at different locations. Applications were done either by drip or drench application which does not have an influence on efficacy. At the specified time (days after first application or days after last application), root health was evaluated.

The results are depicted in the table below:

Bell Pepper

| formulation | Amount applied (amount of spores) | Time of measurement | Efficacy (ABBOT) | No. of applications |
|---|---|---|---|---|
| BioAct WG | 2 kg/ha | 127 d after first application | 13.6 | 4 |
| BioAct DC | 400 ml/ha* | 127 d after first application | 31.8 | 4 |

*equivalent to about $2.2 \times 10^{13}$ spores per hectare

Cucumber

| | Trial 1 | | | |
|---|---|---|---|---|
| formulation | Amount applied | Time of measurement | Efficacy (ABBOT) | No. of applications |
| BioAct WG | 4 kg/ha | 42 d after first application | 37.1 | 4 |
| BioAct DC | 800 ml/ha | 42 d after first application | 40.2 | 4 |

| | Trial 2 | | | |
|---|---|---|---|---|
| formulation | Amount applied | Time of measurement | Efficacy (ABBOT) | No. of applications |
| BioAct WG | 4 kg/ha | 14/34 d after last application | 66.7/51.0 | 2 |
| BioAct DC | 800 ml/ha | 14/34 d after last application | 72.0/75.4 | 2 |

| | Trial 3 | | | |
|---|---|---|---|---|
| formulation | Amount applied | Time of measurement | Efficacy (ABBOT) | No. of applications |
| BioAct WG | 4 kg/ha | 63 d after first application | 44.2 | 3 |

-continued

Trial 3

| formulation | Amount applied | Time of measurement | Efficacy (ABBOT) | No. of applications |
|---|---|---|---|---|
| BioAct DC | 800 ml/ha | 63 d after first application | 47.5 | 3 |

Tomato

Trial 1

| formulation | Amount applied | Time of measurement | Efficacy (ABBOT) | No. of applications |
|---|---|---|---|---|
| BioAct WG | 4 kg/ha | 56/145 d after first application | 54.0/27.2 | 4 |
| BioAct DC | 800 ml/ha | 56/145 d after first application | 49.3/29.1 | 4 |

Trial 2

| formulation | Amount applied | Time of measurement | Efficacy (ABBOT) | No. of applications |
|---|---|---|---|---|
| BioAct WG | 4 kg/ha | 71/140 d after first application | 35.2/34.9 | 4 |
| BioAct DC | 800 ml/ha | 71/140 d after first application | 34.1/37.7 | 4 |

Lettuce

| formulation | Amount applied | Time of measurement | Efficacy (ABBOT) | No. of applications |
|---|---|---|---|---|
| BioAct WG | 4 kg/ha | 51 d after first application | 54.8 | 3 |
| BioAct DC | 800 ml/ha | 51 d after first application | 76.2 | 3 |

EXAMPLE 8

Moisture Content in the Spore Powder Used in the Formulation according to the Invention To create the mixtures a fumed silica (Aerosil 200) was mixed into a polyether-modified trisiloxane (BreakThru S 240) at a ratio of 6:94 applying an Ultra Turax for 10 min at 10,000 rpm and for further 5 min at 5600 rpm.

The resulting liquid then was mixed with *Purpureocillium lilacinum* conidia powder in a way that 18.9 g (moisture content of 9%) or 18.3 g (moisture content of 6%) conidia powder (about $3.3\times10^{11}$ spores/g) were blended into 81.1 grams or 81.7 grams using an Ultra Turrax for 2 min at 5400 rpm. The resulting conidia suspensions contained $5.50\times10^{10}$ viable conidia per gram. Another sample with spores of the fungus *Isaria fumosorosea* was prepared in that 41.9 g conidia powder (about $1.6\times10^{11}$ spores/g) were blended into 58.1 grams each liquid using an Ultra Turrax for 2 min at 5400 rpm. The resulting conidia suspension contained $5.50\times10^{10}$ viable conidia per gram. The conidia suspensions then were filled into 20 ml glass bottles up to 1.5 cm below the top sealed and incubated at 30° C. to evaluate the storage stability of the conidia.

Viability was measured at the time points indicated in tables 6 and 7 below.

TABLE 6

| *Purpureocillium lilacinum* | | |
|---|---|---|
| Time point | Viability % | |
| Moisture content of spore powder % | 9 | 6 |
| initiation | 97 | 98 |
| 4 weeks | 83.6 | 92.8 |

TABLE 7

| *Isaria fumosorosea* | |
|---|---|
| Time point | Viability % |
| Moisture content of spore powder % | 9 |
| initiation | 89.6 |
| 2 weeks | 67.8 |

The invention claimed is:

1. A stable, homogeneous liquid composition comprising at least one biological control agent, wherein said biological control agent is spores of a spore forming fungus, a polyether-modified trisiloxane and fumed silica or precipitated silica, wherein said composition is essentially free of water, wherein the presence of the silica reduces spore sedimentation in comparison to a composition without silica.

2. The composition according to claim 1, which is essentially free of oil.

3. The composition according to claim 1 further comprising an antifoaming agent.

4. The composition according to claim 1, wherein the concentration of said fumed silica or precipitated silica is in the range of 0.1 to 9 wt.-%.

5. The composition of claim 1, wherein said biological control agent is a fungus that exhibits activity against insects, acarids, spiders, nematodes, molluscs, bacteria, rodents, weeds and/or phytopathogens.

6. The composition according to claim 1 further comprising at least one further plant protective agent.

7. The composition according to claim 1, wherein said biological control agent is present in the form of conidia or chlamydospores.

8. The composition according to claim 1, wherein the spores of said spore forming fungus are dried spores.

9. The composition of claim 1, wherein said spores are present in a concentration of between about $1\times10^5$/ml and $2\times10^{11}$/ml.

10. The composition according to claim 1, wherein said biological control agent has fungicidal activity and is selected from *Coniothyrium minitansArthrobotrys dactyloides; Arthrobotrys oligospora; Arthrobotrys superba; Aspergillus flavus, Aspergillus flavus; Gliocladium roseum, Phlebiopsis* (or *Phlebia* or *Peniophora*) *gigantea; Phlebiopsis* (or*Phlebia* or *Peniophora*) *gigantea, Pythium oligandrum, Talaromyces flavus; Ampelomyces quisqualis; Chaetomium cupreum; Chaetomium globosum; Cladosporium cladosporioides; Dactylaria candida; Dilophosphora alopecuri; Fusarium oxysporum; Gliocladium catenulatum; Lecanicillium lecanii* (formerly known as *Verticillium lecanii*) *conidia; Penicillium vermiculatum; Ulocladium oudemansii, Verticillium alboatrum* (formerly *V. dahlia*), *Verticillium chlamydosporium.*

11. The composition according to claim 1, wherein said biological control agent has insecticidal activity and is selected from *Beauveria bassiana* strain ATCC 74040; *Beauveria bassiana* strain GHA (Accession No. ATCC74250; *Beauveria bassiana* strain ATP02 (Accession No. DSM 24665); *Beauveria bassiana* strain CG 716; *Hirsutella citriformis; Hirsutella thompsonii; Lecanicillium lecanii* (formerly known as *Verticillium lecanii*) conidia of strain KV01; *Lecanicillium lecanii* (formerly known as *Verticillium lecanii*) conidia of strain DAOM198499; *Lecanicillium lecanii* (formerly known as *Verticillium lecanii*) conidia of strain DAOM216596; *Lecanicillium muscarium* (formerly *Verticillium lecanii*) strain VE 6 / CABI(=IMI) 268317/CBS102071/ ARSEF5128; *Metarhizium anisopliae* strain F52 (DSM3884/ ATCC 90448; *M. anisopliae var acridum; M. anisopliae var acridum* isolate IMI 330189 *Nomuraea rileyi; Paecilomyces fumosoroseus* (new: *Isaria fumosorosea*) strain apopka 97; *Paecilomyces fumosoroseus*(new: *Isaria fumosorosea*) strain FE 9901; *Aschersonia aleyrodis; Beauveria brongniartii; Metarhizium flavoviride; Mucor haemelis*.

12. The composition according to claim 1, wherein said biological control agent has nematicidal activity and is selected from *Paecilomyces lilacinus* strain 251; *Trichoderma koningii; Harposporium anguillullae; Harposporium anguillullae; Monacrosporium cionopagum; Monacrosporium psychrophilum; Myrothecium verrucaria* strain AARC-0255; *Stagonospora*phaseoli; Trichoderma lignorum strain TL-0601; *Fusarium solani* strain Fs5; *Hirsutella rhossiliensis; Monacrosporium drechsleri; Monacrosporium gephyropagum; Nematoctonus geogenius; Nematoctonus leiosporus; Pochonia chlamydospora* (also known as *Vercillium chlamydosporium*) var. *catenulata* IMI SD 187, CU; *Stagonospora heteroderae; Meristacrum asterospermum* and *Duddingtonia flagrans*.

13. The composition according to claim 1, wherein said biological control agent which supports and/or promotes and/or stimulates plant health and plant growth and is *Penicillium bilaii*.

14. The composition according to claim 1, wherein said biological control agent is spores of Paecilomyces lilacinus.

15. The composition according to claim 14, wherein said Paecilomyces lilacinus is Paecilomyces lilacinus strain 251 or a mutant thereof.

16. The composition according to claim 1, wherein the amount of polyether-modified trisiloxane ranges between 50 and 96% wt.

17. A method of producing a composition according to claim 1, comprising the steps of providing a carrier comprising a polyether-modified trisiloxane and fumed silica or precipitated silica in a concentration that in the final composition results in a concentration of between 50 and 96% wt polyether-modified trisiloxane and between about 0.1 and 9% wt fumed silica or precipitated silica, and incorporating a biological control agent into said carrier, wherein said biological control agent is spores of a spore forming fungus.

18. A method for controlling phytopathogenic fungi, insects, spiders, molluscs, weeds, rodents and/or nematodes in a plant, for enhancing growth of a plant or for increasing plant yield or root health comprising applying the composition of any one of claims 1 to 16 to said plant or to a plot where plants are to be grown.

19. The composition according to claim 1, wherein said biological control agent is selected from *Coniothyrium minitans* strain CON/M/91-8 (Accession No. DSM-9660); *Microsphaeropsis ochracea* strain P130A (ATCC deposit 74412) *Trichoderma atroviride*, strain SC1; *Trichoderma harzianum rifai* strain KRL-AG2; *Aspergillus flavus*, strain NRRL 21882; *Aspergillus flavus*, strain AF36; *Gliocladium roseum*, strain 321U; B2.15 *Phlebiopsis* (or *Phlebia* or *Peniophora*) *gigantea* strain VRA 1835 (ATCC 90304); *Phlebiopsis* (or *Phlebia* or *Peniophora*) *gigantea* strain VRA 1984 (DSM16201); *Phlebiopsis* (or *Phlebia* or *Peniophora*) *gigantea* strain VRA 1985 (DSM16202); *Phlebiopsis* (or *Phlebia* or *Peniophora*) *gigantea* strain VRA 1986 (DSM16203); *Phlebiopsis* (or *Phlebia* or or *Peniophora*) *gigantea* strain FOC PG B20/5 (IMI390096); *Phlebiopsis* (or *Phlebia* or *Peniophora*) *gigantea* strain FOC PG SP 1og6 (IMI390097); *Phlebiopsis*(or *Phlebia* or*Peniophora*) *gigantea* strain FOC PG SP 1og5 (IMI390098); *Phlebiopsis* (or *Phlebia* or *Peniophora*) *gigantea* strain FOC PG BU3 (IMI390099); *Phlebiopsis*(or *Phlebia* or *Peniophora*) *gigantea* strain FOC PG BU4 (IMI390100); *Phlebiopsis*(or *Phlebia* or *Peniophora*) *gigantea* strain FOC PG 410.3 (IMI390101); *Phlebiopsis*(or *Phlebia* or *Peniophora*) *gigantea* strain FOC PG 97/1062/116/1.1 (IMI390102); *Phlebiopsis*(or *Phlebia* or *Peniophora*) *gigantea* strain FOC PG B22/SP1287/3.1 (IMI390103); *Phlebiopsis*(or *Phlebia* or *Peniophora*) *gigantea* strain FOC PG SH1 (IMI390104); *Phlebiopsis*(or *Phlebia* or *Peniophora*) *gigantean*strain FOC PG B22/SP1190/3.2 (IMI390105); *Pythium oligandrum* strain DV74 or M1 (ATCC 38472); *Talaromyces flavus* strain VII7b; *Trichoderma asperellum* strain ICC 012; *Trichoderma asperellum*strain SKT-1; *Trichoderma atroviride* strain CNCM 1-1237; *Trichoderma atroviride*strain no. V08/002387; *Trichoderma atroviride* strain NMI no. V08/002388; *Trichoderma atroviride*strain NMI no. V08/002389; *Trichoderma atroviride* strain NMI no. V08/002390; *Trichoderma atroviride* strain LC52; *Trichoderma atroviride* strain ATCC 20476 (IMI 206040); *Trichoderma atroviride* strain T11 (IMI352941/ CECT20498); *Trichoderma harmatum; Trichoderma harzianum; Trichoderma harzianum rifai* T39; *Trichoderma harzianum* strain KD; *Trichoderma harzianum* strain ITEM 908; *Trichoderma harzianum* strain TH35; *Trichoderma virens* (also known as *Gliocladium virens* strain GL-21; *Trichoderma viride*, strain TV1; *Ampelomyces quisqualis* strain AQ 10; *Cladosporium cladosporioides*strain H39; *Dactylaria candida; Dilophosphora alopecuri; Fusarium oxysporum* strain Fo47; *Gliocladium catenulatum* (Synonym: *Clonostachys rosea f. catenulate*) strain J1446; *Lecanicillium lecanii* (formerly known as *Verticillium lecanii*) conidia of strain KV01; *Trichoderma atroviride* strain SKT-1 (FERM P-16510); *Trichoderma atroviride* strain SKT-2 (FERM P-16511); *Trichoderma atroviride* strain SKT-3 (FERM P-17021); *Trichoderma gamsii* (formerly *T. viride*) strain ICC080; *Trichoderma harzianum* strain DB 103; *Trichoderma polysporum* strain IMI 206039; *Trichoderma stromaticum; Ulocladium oudemansii* strain *HRU*3; *Verticillium albo-atrum* (formerly *V. dahlia*) strain WCS850; and mixtures of *Trichoderma asperellum* strain ICC 012 and *Trichoderma gamsii* strain ICC 080 (product known as e.g., BIO-TAM™from Bayer CropScience LP, US).

20. The composition according to claim 13, wherein said *Penicillium bilaii* is *Penicillium bilaii* strain ATCC 22348 or a mutant thereof.

21. The composition according to any one of claims 1 through 4 comprising 8 wt-% or less water.

* * * * *